United States Patent
Mahood

(10) Patent No.: US 8,247,619 B2
(45) Date of Patent: Aug. 21, 2012

(54) BPA AND POLYCARBONATE MADE FROM RENEWABLE MATERIALS

(75) Inventor: James A. Mahood, Evansville, IN (US)

(73) Assignee: Sabic Innovative Plastics IP B.V., Bergen Op Zoom (NL)

( * ) Notice: Subject to any disclaimer, the term of this patent is extended or adjusted under 35 U.S.C. 154(b) by 252 days.

(21) Appl. No.: 12/636,695

(22) Filed: Dec. 11, 2009

(65) Prior Publication Data

US 2010/0152406 A1    Jun. 17, 2010

Related U.S. Application Data

(60) Provisional application No. 61/121,663, filed on Dec. 11, 2008.

(51) Int. Cl.
C07C 37/16 (2006.01)
(52) U.S. Cl. ........................................ 568/727
(58) Field of Classification Search .................. 568/727
See application file for complete search history.

(56) References Cited

U.S. PATENT DOCUMENTS

| | | | |
|---|---|---|---|
| 3,153,008 A | 10/1964 | Fox | |
| 3,375,210 A | 3/1968 | D'Onofrio | |
| 3,437,637 A | 4/1969 | Matzner et al. | |
| 4,156,098 A | 5/1979 | Li | |
| 4,352,945 A | 10/1982 | Bezman | |
| 4,375,567 A | 3/1983 | Faler | |
| 4,387,251 A | 6/1983 | Meyer et al. | |
| 4,420,644 A | 12/1983 | Huibers et al. | |
| 4,605,790 A | 8/1986 | Wojtkowski | |
| 4,647,704 A | 3/1987 | Engel et al. | |
| 4,814,520 A | 3/1989 | Nakagawa | |
| 4,857,151 A | 8/1989 | Suciu et al. | |
| 4,900,873 A | 2/1990 | Kakemoto et al. | |
| 4,962,240 A | 10/1990 | Kitamura et al. | |
| 5,064,507 A | 11/1991 | O'Donnell et al. | |
| 5,087,767 A | 2/1992 | Okamoto et al. | |
| 5,248,839 A | 9/1993 | Iimuro et al. | |
| 6,784,324 B2 | 8/2004 | Saruwatari | |
| 6,872,858 B2 | 3/2005 | Muragaki et al. | |
| 6,939,994 B1 | 9/2005 | Smith, Jr. et al. | |
| 7,491,346 B2 | 2/2009 | Hikosaka | |
| 2009/0117478 A1 | 5/2009 | Ogawa | |

OTHER PUBLICATIONS

Database CAPLUS on STN, Acc. No. 1988:122051, Sakamoto et al., JP 62186201 A (Aug. 14, 1987) (abstract).*
Wierckx et al, "Engineering of Solvent-Tolerant Pseudomonas putida S12 for Bioproduction of Phenol from Glucose", Applied and Environmental Microbiology, Dec. 2005, pp. 8221-8227, vol. 71, No. 12.
Nakagawa et al."Material for Optical Appliance", English abstract of Japanese Patent No. 61255929, Nov. 13, 1986.
Sakamoto et al."Stock for Optical Apparatus", English abstract of Japanese Patent No. 62186201, Aug. 14, 1987.
Sakamoto et al."Optical Material", English abstract of Japanese Patent No. 1029422, Jan. 31, 1989.

* cited by examiner

Primary Examiner — Brian J Davis
(74) Attorney, Agent, or Firm — Larson & Anderson, LLC

(57) ABSTRACT

Bio-derived bisphenol A is made by combining bio-derived phenol and/or bio-derived acetone in the presence of a catalyst, The phenol or the acetone or both contain at least 0.5%, for example at least 1 weight % of bio-derived impurities. In the case of bio-derived phenol, these impurities may include one or more of 2-methylbenzofuran, 2-methoxyphenol, 2-methylphenol, 4-methylphenol (para-cresol) or 2-methoxy-4-methylphenol. In the case of acetone, the impurity may be ethanol, mesityl acetone and/or diacetone alcohol. This bio-derived BPA can be used in the production of polycarbonates with less fossil fuel-based carbon content.

26 Claims, No Drawings

BPA AND POLYCARBONATE MADE FROM RENEWABLE MATERIALS

This application claims the benefit of U.S. Provisional Application No. 61/121,663 filed Dec. 11, 2008, which application is incorporated herein by reference in its entirety.

BACKGROUND OF THE INVENTION

Polycarbonates are used in many commercial and industrial applications because of their strength and other properties. Of particular importance are BPA-polycarbonates formed in whole or in part from bisphenol A (BPA) monomers.

BPA is commonly formed from the reaction of phenol and acetone. For example, U.S. Pat. Nos. 4,156,098, 4,375,567, 5,087,767, 5,248,839, 6,784,324, and 6,939,994 disclose processes for making BPA from phenol and acetone. In the adduct-crystallization method, acetone is reacted with excess phenol over an acidic IER (Ion Exchange Resin) catalyst bed. The product solution is cooled and BPA crystallizes out as a phenol adduct. The solid BPA adduct is removed by filtration. Most of the filtrate is recycled to the reactor although a portion is purged from the system. The BPA adduct is then melted and stripped of phenol in a desorber. Recovered phenol is recycled to the reactor and the clean BPA is then sent forward to polymerization.

Phenol can be made from the partial oxidation of benzene or benzoic acid, by the cumene process, by the catalytic dehydrogenation of cyclohexanone or cyclohexanol or by the Raschig process. It can also be found as a product of coal oxidation. Phenol used in the production of BPA today is typically greater than 99.9% purity and is derived from fossil fuel sources (petroleum or coal). The rising costs of such products, and their non-renewable nature makes these routes to the preparation of phenol less desirable. Thus, there is interest in preparation of phenols from renewable sources. For example, U.S. Pat. Nos. 4,420,644 and 4,647,704 describe catalyzed hydrocracking of lignin to produce phenol and other products. U.S. Pat. No. 4,900,873 discloses preparation of phenolic compounds by thermal decomposition of a lignin-containing material. Addition of double ring aromatic hydrocarbons such as naphthalene or biphenyl is taught to increase the yield of phenolic products. U.S. Pat. No. 4,605,790 describes a process for the preparation of phenol from mixed phenols obtained from coal or biomass. Frost et al, Angew. Chem. Int. Ed., 2001, 40(10) p 1945-1948 describes a shikimic acid bio-route to phenol. The preparation of phenol from glucose has also been described. (Applied and Environmental Microbiology, 2005, 71(12), p 8221-8227.

Acetone for bulk synthetic applications is also similarly derived from fossil sources. Acetone is commonly made by the Hock process wherein cumene is hydroperoxidated and then cleaved to form phenol and acetone. In some cases, the phenol and acetone can be directly reacted without intermediate purification to produce a BPA end product. Acetone is also made commercially from oxidation of isopropanol, which in turn can be produced from hydration of propylene. (see, for example, U.S. Pat. No. 4,352,945).

Acetone can also be derived from renewable sources, for example by reaction from bio-derived ethanol, or by fermentation processes. Bioacetone made by fermentation shows similar impurities as found in cumene-derived acetone by GC determination ((mesityl oxide and diacetone alcohol) both at <100 ppm levels). Bioacetone has also been made from pyrolysis of calcium acetate at 430-490° C. (Industrial and Engineering Chemistry, 1924, p 1133-1139) or more reasonably from Hock oxidative cleavage of terpene-derived p-cymene ('Catalytic aspects in the transformation of pinenes to p-cymene', APPLIED CATALYSIS A: GENERAL 215 (2001) p 111-124), but neither of these routes to acetone appears to be commercially practiced or feasible to acetone.

It would be desirable to be able to make BPA, and then polycarbonates from bio-derived phenol and/or acetone, or from bio-derived cumene in order to make materials incorporating BPA, including polycarbonates less dependent on fossil fuels.

SUMMARY OF THE INVENTION

The present invention provides a method for preparing bisphenol A comprising combining phenol and acetone in the presence of a catalyst to form bisphenol A, wherein the phenol or the acetone or both contain at least 0.5%, for example at least 1 weight % of bioderived impurities. In the case of bioderived phenol, these impurities may include one or more of 2-methylbenzofuran, 2-methoxyphenol, 2-methylphenol, 4-methylphenol (para-cresol) or 2-methoxy-4-methylphenol. In the case of acetone, this impurity may be ethanol, mesityl acetone and/or diacetone alcohol. This bio-derived BPA can be used in the production of polycarbonates with less fossil fuel-based carbon content.

DETAILED DESCRIPTION OF THE INVENTION

While the goal of utilizing bio-derived materials in place of fossil-fuel derived materials is an easy one to state, the actual implementation is not so straight forward. In many cases, bioderived materials will have impurities in greater amounts and/or of different types from the same fossil-fuel derived matter. Purification of the material is of course an option, but this purification can require so much energy to achieve that more fossil fuel is used for energy than would have been used as a feedstock. For this reason, bio-derived materials such as biophenol are commonly employed in resins and adhesives which have greater tolerance for these impurities. However, for use in polycarbonates, which are used in many cases because of particular optical and physical properties, these impurities might be expected to lead to various difficulties in subsequent processing to form polycarbonates, including without limitation: unacceptable color or clarity, unacceptable branching if polyhydric materials are present as impurities, and poor control over molecular weight growth if variable amounts of mono-hydric impurities that act as chain stoppers are present. Purification efforts are costly and thus incompatible with large volume products such as BPA and polycarbonates. Indeed expensive purification might well use more fossil fuel materials to supply energy than the cumene process uses as a feedstock. With this in mind, the present inventors have performed experiments to determine the best approaches to making BPA, and then polycarbonate, from bio-derived materials. This study provides an understanding that certain impurities are of more significance than others, and that some impurities are readily removed as part of processing techniques. Thus, the present invention provides a method for making BPA, and using that BPA to make polycarbonates in which one or more feedstocks containing measurable amounts of bio-derived impurities are utilized.

As used in this application, the term "bio-derived" refers to acetone and/or phenol from a currently renewable resource, as opposed to fossil fuels. This can be verified by measurements on carbon isotope levels, since the relative amounts of isotopic carbon are lower in fossil-fuel materials.

The most common impurities found in biophenol are 2-methylphenol (o-cresol), 2-methylbenzofuran, 4-methylphenol (para-cresol), and 2-methoxy-4-methylphenol. The most common impurities in bioacetone are ethanol, mesityl acetone and diacetone alcohol.

To evaluate the importance of the various impurities, experiments were performed as follows:

(a) Phenol Spiking Experiments

Cumene-derived phenol was spiked with an impurity and processed through a standard adduct-crystallization BPA synthesis with an IER catalyst with attached promoter, in a downflow continuous reactor with 4% acetone in the feed. The weighted hourly space velocity was about 0.8 at 70° C. The reaction product was crystallized at 50° C. and the resulting BPA adduct was isolated by filtration at 50° C. and washed with clean phenol. The BPA adduct was then heated under nitrogen to about 120° C. to give a molten material that was stripped to about 170° C. under about 15 torr vacuum to remove monophenols. The molten BPA was then poured into a glass dish at room temperature where it crystallized within seconds. LC analysis was performed on both the adduct and the adduct filtrate.

The solid BPA was then used to make BPA PC under standard interfacial conditions. 25-35 g BPA, 500 ml $CH_2Cl_2$, 300 ml water, 0.2 ml triethylamine, and 3 m % phenol endcap were charged to a 2 L Morton flask equipped with a phosgene inlet, reflux condenser with caustic scrubber, caustic solution inlet, pH probe and controller and mechanical agitation. Phosgene was added subsurface at 2 g/min while a 50 wt % caustic solution was added at a rate sufficient to maintain the pH at about 9. The phosgene charge was adjusted to 140% of theory based on the amount of BPA charged. After the phosgene charge was complete, the reactor was purged with nitrogen for 10 minutes. Then stirring was stopped and the phases allowed to separate. The bottom $CH_2Cl_2$ layer was removed from the reactor and washed with 1N HCl (1×500 ml) and then with deionized water (3×500 ml). The polymer was isolated by hot water precipitation and dried overnight at 70° C.

(b) BPA Color Stability

Samples of BPA prepared with different impurities were tested for color stability by oven aging the BPA powder at 140° C. for 5 hours. Absorbance at 350 nm before (IA) and after (FA) aging was measured.

(c) Competitive Adduct Formation

A competitive experiment was conducted to see which phenolic impurities in biophenol could form adducts with BPA in the same manner as phenol. BPA was dissolved in a mixture of phenol and the impurity at 100° C. and then cooled to 50° C. and held overnight to allow adduct formation. Solids were isolated by filtration, washed with toluene to remove surface contamination and analyzed by UPLC.

(d) PC Color Stability

Polycarbonate prepared from BPA with added impurity and 0.06 parts per hundred IRGAPHOS 168 stabilizer and extruded on a twin screw extruder before molding into 125 mil color chips. The chips were aged at 80° C. or 120° C. for 1000 hours and the color shift (YI(final)−YI(initial)) was observed.

The results of these experiments are discussed for each impurity.

O-cresol

O-cresol was found as an impurity in an amount of about 0.06 wt % in a commercially purchased highly purified sample of biophenol.

A phenol spiking experiment was conducted using 5 wt % o-cresol spiked into cumene-derived phenol and run through the standard BPA synthesis, isolation, and polymerization sequence. LC analyses of the adduct and adduct filtrate were quite clean and showed the presence of significant amounts of a new material (probably monomethyl-BPA, a BPA analog where one phenol ring has been replaced with an o-cresol ring). Some free o-cresol was present in the adduct but the amount was fairly small. The free o-cresol was removed during the adduct stripping step but the o-cresol reaction product remained. This indicates that o-cresol impurities in the incoming bio-phenol stream would result in low levels of monomethyl BPA impurity. The effect of such an impurity on BPA PC physical properties should be minimal, although there may be an increase in color or in color shift on aging. At high levels, this impurity could also have the effect of depressing Tg and reducing ductility.

As shown in Table 1, the BPA color stability test showed both a higher initial coloration and greater color formation as compared to BPA made without the impurity.

TABLE 1

| Material | IA | FA |
| --- | --- | --- |
| Control BPA (no spiking) | 0.1981 | 0.4534 |
| o-cresol spiked rxn product | 0.2398 | 0.9252 | o-Cresol was combined with phenol and BPA in a weight ratio of 45:45:25 for the competitive adduct formation test. The adduct yield at 50° C. was 14.6 g, substantially lower than for phenol (90:25) or p-cresol and phenol (45:45:25), both of which had a yield of 23.3 grams. Thus, o-cresol apparently interferes with BPA adduct formation, such that when an adduct crystallization process is used as part of the BPA purification process, the presence of high levels of o-cresol may negatively impact product yield. The adduct, as determined by peak area at 282 nm, contained 85.46% BPA, 11.07% phenol and 3.47% o-cresol by weight.

Based on these tests, it is apparent that while o-cresol is of some concern, the very high purification of the commercial sample is not required. In general, o-cresol impurity levels of greater than 0.25%, for example greater than 0.5 wt % and even greater than 1.0 wt % can be tolerated. For applications where color in the BPA or polycarbonate product is an issue, amounts of o-cresol less than 5%, preferably less than 4% and more preferably less than 3% are preferred. If color is not an issue, such as in the manufacture of opaque automobile body parts, even higher levels of o-cresol can be tolerated, for example up to 10, 15, or 20 wt %.

2-Methylbenzofuran

2-Methylbenzofuran (2-MBF) was found in the commercially available sample of biophenol at a level of 0.01 wt %. The presence of 2-MBF in phenol is known to contribute to high color in BPA and BPA polycarbonates. Typical levels in fossil fuel-derived phenol are <50 ppm and 'good' phenol will have <10 ppm. Thus, 2-MBF is present in even the very highly purified biophenol at levels in excess of what is normally considered acceptable for the production of BPA.

Some current plants have an entire distillation column devoted to removing 2-MBF and related materials. Since 2-MBF cannot be removed from dry phenol by simple distillation, a special distillation column is used where water is added to essentially steam strip out the 2-MBF and related impurities. Inclusion of such a purification column in a manufacturing process utilizing biophenol may therefore be necessary. See U.S. Pat. Nos. 5,064,507 and 4,857,151.

To confirm the importance of 2-MBF, a phenol spiking experiment was conducted using 6.64 g 2-MBF in 2214.2 g phenol, or 0.3 wt % spiked into cumene-derived phenol and run through the standard BPA synthesis, isolation, and polymerization sequence. No free 2-MBF was detected in the reaction product, although 3 new MBF reaction products were observed. Two of these reaction products are removed in the phenol desorption step, but the other remained and moved forward to the polymerization step.

The solid BPA adduct was visually pink and contained 66.34% BPA, 32.69% phenol, and 0.95% unknown (retention time 1.14 minutes). A known standard of 2-MBF was injected using the same UPLC method and showed a retention time of 1.60 minutes, indicating the unknown peak was not unreacted 2-MBF. This unknown peak was absent in control samples run without the 2-MBF spiking.

To determine the effect of 2-MBF on PC color formation, a PC color formation test was done with 725 ppm 2-MBF. The results are summarized in Table 2

TABLE 2

| Material | YI shift 80 deg C. | YI shift 120 deg C. |
| --- | --- | --- |
| Control | 0.72 | 2.37 |
| 2-MBF | 0.67 | 2.59 |

Thus, it appears that the 2-MBF itself is not a significant contributor to the color formation, and that it is the unknown reaction product that is of concern.

As shown in Table 3, the BPA color stability test on the material made with 2-MBF showed both a slightly lower initial coloration (yellow) and a greater color formation as compared to BPA made without the impurity.

TABLE 3

| Material | IA | FA |
| --- | --- | --- |
| Control BPA (no spiking) | 0.1981 | 0.4534 |
| 2-MBF spiked rxn product | 0.1848 | 0.5520 |

From this information, it can be concluded that 2-MBF doesn't cause a lot of color by itself. Instead, it is one of the reaction products of 2-MBF that lead to a pink BPA and polymer. This reaction product does not seem to be removed during adduct formation so the 2-MBF levels in biophenol need to be less than the spiked level of 0.3 wt % for use in low color BPA PC.

P-cresol

P-cresol is expected to be less reactive than phenol in the BPA synthesis reaction as the para location is typically the most reactive in BPA synthesis and this is unavailable for reaction in p-cresol. Nevertheless, detectable levels of the p-cresol analog of o,p-BPA would be expected, as there is no clear reason that the analogous chemistry could not occur. The o,p-BPA is an undesirable impurity in BPA as the more hindered phenolic group sometimes survives interfacial phosgenation without reacting and functions as a color-forming endcap. In addition, as a monophenol, free para-cresol can function as an endcapper (chain terminator) if carried forward to the polymerization reaction.

A spiking experiment was performed in which 4 wt % p-cresol was added to cumene-derived phenol. The resulting solid BPA adduct was analyzed by UPLC. The UPLC was not specifically calibrated for these materials and the levels were based on simple % peak area. The adduct was 71.44% BPA, 28.01% phenol, and 0.53% p-cresol, suggesting p-cresol was forming a BPA adduct similar to the BPA-phenol adduct. Surprisingly, no signs of any p-cresol reaction products were detected in the BPA adduct.

UPLC analysis of the corresponding adduct filtrate showed significant amounts of p-cresol and two new peaks that were not observed in control experiments. These peaks were too small to easily identify (well under 1%), so an additional spiking experiment was carried out with even higher levels of p-cresol to try to increase the amount of impurities formed.

An approximately 50/50 mix of phenol and p-cresol was reacted with acetone in a continuous IER reactor. BPA adduct and filtrate were isolated as before. Even at these high p-cresol levels the reaction produced good BPA, but the levels of the two new impurities in the adduct filtrate were increased to ~1% (unknown with retention time 1.64 min) and ~0.2% (unknown with retention time 0.72 min).

This data suggests that a significant portion of any p-cresol impurity would move forward past the BPA adduct filtration into the phenol desorption step. Given similar volatility to phenol, the desorber should effectively remove p-cresol to very low levels. The UPLC analysis of the BPA adduct showed no detectable free p-cresol, so the p-cresol was removed very effectively during the desorption step.

Color stability testing was performed to determine the consequences of failure to remove p-cresol during BPA purification. p-Cresol was spiked into BPA at levels of 500 ppm and 2,500 ppm and converted into BPA polycarbonate. The color stability results are summarized in Table 4

TABLE 4

| Material | YI shift 80 deg C. | YI shift 120 deg C. |
| --- | --- | --- |
| Control BPA PC | 0.72 | 2.37 |
| p-cresol 500 ppm spike | 0.69 | 2.33 |
| p-cresol 2500 ppm spike | 0.90 | 3.06 |

From this it can be seen that p-cresol at the higher level may lead to color issues with aging, but that levels of 500 ppm are the same as the control.

p-Cresol was combined with phenol and BPA in a weight ratio of 45:45:25 for the competitive adduct formation test. The adduct yield at 50° C. was 23.3 g, the same as for phenol alone. The adduct, as determined by peak area at 282 nm contained 63.48% BPA, 0.99% phenol and 35.53% p-cresol by weight. Thus, surprisingly, BPA formed an adduct with p-cresol to the exclusion of forming the standard phenol adduct. p-Cresol present as an impurity in biophenol does not readily react with acetone due to the blocked para-position, so most of the p-cresol will enter the adduct crystallization stage as free p-cresol. Assuming it precipitates as the BPA adduct, the p-cresol would move to the stripping step where it was readily removed from the BPA.

As is clear from the previous experiments, p-cresol may constitute an impurity at levels of at least 500 ppm (0.05 wt %) with no detrimental effect on BPA and may be present at higher levels, for example more than 0.10, 0.25, 0.50, 1.0, 5.0 or 10.0 wt %, particularly where color is not an issue in the product.

2-Methoxy-4-methylphenol

2-Methoxy-4-methylphenol is another contaminant found in bio-derived phenol. It is structurally very similar to p-cresol, but with one ortho-position blocked, this material was expected to be even less reactive than p-cresol.

Again, a spiking experiment was performed, loading 2.6 wt % 2-methoxy-4-methylphenol. This gave no new detectable peaks in the BPA adduct, suggesting this material did not form an adduct with BPA. UPLC analysis of the filtrate showed significant levels of unreacted 2-methoxy-4-methylphenol but no peaks that could be attributed to 2-methoxy-4-methylphenol reaction products. This indicates that 2-methoxy-4-methylphenol would not affect final BPA quality, and purification of this material is not required.

Guaiacol (2-methoxyphenol):

Guaiacol is not found in cumene-derived phenol but may be found in bio-derived phenol.

A phenol spiking experiment was conducted using 5 wt % guaiacol was spiked into cumene-derived phenol and run through the standard BPA synthesis, isolation, and polymerization sequence. Free guaiacol was detected in the BPA adduct, along with two new guaiacol reaction products. The free guaiacol was removed cleanly during the adduct strip step.

In the competitive adduct formation test, no solids were observed in the guaiacol experiment, indicating that guaiacol strongly inhibited adduct formation. This would obviously be a serious issue if the guaiacol levels were high in an incoming biophenol stream or if guaiacol was allowed to accumulate in a recycle stream.

As shown in Table 5, the BPA color stability test showed that color properties were actually better in the presence of the guaiacol impurity to the extent that the differences are in fact significant.

TABLE 5

| Material | IA | FA |
|---|---|---|
| Control BPA (no spiking) | 0.1981 | 0.4534 |
| Guaiacol spiked rxn product | 0.1769 | 0.3472 |

From the foregoing, it can be seem that the key concern with guaiacol is the effect on adduct formation, when this is the synthetic process used. In this case, it is desirable to limit the amount of guaiacol to less than 15%, preferably less than 10% and more preferably less than 5% of the biophenol stream. Where other synthetic processes are used, purification with respect to guaiacol may be unnecessary.

Bio-Acetone:

Bioacetone shows similar impurities as found in cumene-derived acetone by GC ((mesityl oxide and diacetone alcohol) both at <100 ppm levels), along with 0.2 wt % ethanol that is not found in cumene-derived acetone. Bioacetone was used together with cumene-derived phenol, following the standard BPA synthesis, isolation and polymerization sequence. No new reaction products were observed and no impurities were observed by UPLC in the final BPA. In summary, while impurities found in bio-derived phenol may present issues to the quality of the product, these issues are not so great that extreme purification needs to be pursued making the process uneconomical. Thus, as a general matter, total bio-derived impurities in excess of 0.5%, 1%, 5% or even 25% are permissible, provided that the specific considerations taken into account in Table 6 are taken into account.

TABLE 6

| Impurity | For color-sensitive application | For color-insenstive applications. |
|---|---|---|
| o-cresol | up to 1 wt % | up to 20 wt % |
| 2-MBF | Less than 0.3 wt % | less than 5 wt % |
| p-cresol | less than 0.2 wt % | less than 10 weight % |
| 2-methoxy-4-methylphenol | no particular limit | no particular limit |

TABLE 6-continued

| Impurity | For color-sensitive application | For color-insenstive applications. |
|---|---|---|
| guaiacol | low enough not to inhibit adduct formation | low enough not to inhibit adduct formation |

For the experiments described above, Bio-phenol derived from the destructive distillation of wood tar was purchased from CHANG TING.

Bio-acetone was purchased from PENTA MANUFACTURING. Certified Natural acetone was also purchased from ALDRICH.

Bio-derived BPA was prepared from bio-phenol and bio-acetone using a modified version of the BPA synthesis described in U.S. Pat. No. 4,387,251.

Sustainable polycarbonate was prepared from bio-derived BPA and fossil-derived phosgene. Bio-phenol was used as an endcap to maximize bio-content. The desired polymer structure was confirmed by 1H NMR.

Samples of bio-phenol, bio-acetone, bio-BPA and bio-PC along with appropriate controls were sent to an outside lab for ASTM 6866 testing to quantify bio-content with the following results:

| Sample | Mean Biobased Content |
|---|---|
| Standard Acetone | 0 ± 3% |
| Bio acetone | 98 ± 3% |
| Standard Phenol | 0 ± 3% |
| Biophenol | 100 ± 3% |
| Standard BPA | 0 ± 3% |
| Bio BPA (made from bio-phenol and bio-acetone) | 100 ± 3% |
| Standard BPA PC | 1 ± 3% |
| Bio BPA PC | 91 ± 3% |

Manufacture of Polycarbonates

BPA made in accordance with the method of the invention using bio-derived components, particularly bio-derived phenol and/or bioacetone is used in the synthesis of polycarbonates, including polyestercarbonates, in place of fossil-derived BPA (all or a part of) in any known method, including melt polymerizations, interfacial polymerization and solid state syntheses. The product of such polymerizations is a bio-derived polycarbonate. If bio-derived phenol is used with fossil-derived acetone, BPA having 80% of bio-derived carbons can be achieved. If bio-derived acetone is used as well, the BPA can be made from 100% bio-derived material. When polycarbonate is formed from the BPA, an additional carbon atom is added for each BPA moiety. Thus, the percentage of bio-derived carbons in polycarbonate formed from BPA formed from bio-derived phenol and or acetone will also depend on the source of this carbon, whether it comes from phosgene or a carbonate reactant.

In many synthetic approaches, formation of polycarbonates can be viewed as the reaction of a bisphenol reagent with a linking reagent such as phosgene or a carbonate. In accordance with some embodiments of the invention the bisphenol reagent consists of 80 to 99.9 wt % Bisphenol A and 0.1% to 20% guaiacol bisphenol A, more preferably 80 to 99.0 wt % Bisphenol A and 1% to 20% guaiacol bisphenol A, A further aspect of the invention is BPA-containing polycarbonate in which at least 80%, 90% 95% or 100% of the BPA incorporated in the polymer is bio-derived material. In one embodiment, the BPA-containing polycarbonate is the homopolymer.

A further aspect of the invention is BPA-containing polycarbonate in which the carbon atoms in the polycarbonate are at least 70, 75, 80, 85, 90, or 95 bio-derived carbons.

Synthesis of BPA from Bio-Acetone and Fossil-Derived Phenol

Molten phenol containing 4.3 wt % bio-acetone was fed downflow to a jacketed reactor containing 35 g of attached promoter IER catalyst (a monodispersed strongly acidic ion exchange resin with 2% divinylbenzene crosslinking, modified with ethylmercaptan promoter, 2.2 meg strong acid/g, 1.4 meg SH/g) with weighted hourly space velocity of 0.8 while the reactor was held at 70° C.

No loss of activity was noted during an eight-day continuous run.

Portions of the reactor output were periodically collected and crystallized at 50° C. The resulting BPA-phenol adduct was isolated by filtration at 50° C. and the filter cake was washed with clean phenol. The BPA-phenol adduct was then heated under nitrogen to about 120° C. to give a molten material that was stripped to 170° C. under about 15 torr vacuum to remove phenol. The molten BPA was then poured into a glass dish at room temperature where it crystallized within seconds.

Synthesis of PC from Bioacetone-Derived BPA

Methylene chloride (20 L), water (12 L), bioacetone-derived BPA (3650 g, 16.0 mol), p-cumylphenol (135 g, 0.64 mol), triethylamine (30 ml) and sodium gluconate (10 g) was charged to a 75 L reactor equipped with mechanical agitation, condenser, and caustic scrubber vent system. Phosgene (2200 g, 22.2 mol) was added at a rate of 80 g/min to the reactor while 33 wt % caustic was added at a rate to maintain pH=9.

The reactor contents were purged with nitrogen then transferred to another tank and centrifuged to remove the brine layer. The organic layer containing the polymer was washed on a centrifuge train with 1N HCl and then with deionized water until residual chloride levels were <5 ppm. The polymer was isolated by steam precipitation followed by drying under hot nitrogen. The final dried resin weighed 6.2 lbs, had Mw=21903 daltons and PDI=2.6 by GPC vs PC standard, <1 ppm TEA, 1.3 ppm chloride ion, <10 ppm residual free BPA, and <0.05 ppm Fe.

The resulting polymer has a predicted bio-derived carbon content (biocontent) of 17 to 19%.

Synthesis of BPA from Bioacetone and Biophenol

Same procedure as for BPA bioacetone and fossil-derived phenol, but using bio-derived phenol.

Synthesis of PC from Bioacetone/Biophenol-Derived BPA

Run 1: Methylene chloride (500 ml), deionized water (300 ml), BPA (28.1 g, 0.123 mol), p-cumylphenol (0.35 g, 0.0017 mol) and triethylamine (0.17 ml) were charged to a 2 L Morton flask equipped with mechanical agitation, pH controller, and chilled glycol condenser operating at 10-15 C. Gaseous phosgene (20 g, 0.20 mol) was introduced subsurface at 2 g/min. Aqueous 50 wt % NaOH was added as necessary to maintain reactor pH=9. The reactor was purged with nitrogen and the absence of residual phosgene confirmed with test paper. Agitation was stopped and the phases allowed to separate. The polymer-containing methylene chloride phase was removed and washed with 1N aqueous HCL (1×500 ml) and then with deionized water (3×500 ml). The polymer was isolated by hot water precipitation and the resulting resin powder was dried in air at 60 C overnight. The resulting polymer had Mw=25950 daltons by GPC vs PC standard.

Run 2: Methylene chloride (13 L), water (13 L), bioacetone/biophenol-derived BPA (2800 g, 12.3 mol), biophenol (36.5 g, 0.39 mol), triethylamine (20 ml) and sodium gluconate (5 g) was charged to a 75 L reactor equipped with mechanical agitation, condenser, and caustic scrubber vent system. Phosgene (1600 g, 16.2 mol) was added at a rate of 80 g/min to the reactor while 50 wt % caustic was added at a rate to maintain pH=9. The reactor contents were purged with nitrogen then transferred to another tank and centrifuged to remove the brine layer. The organic layer containing the polymer was washed on a centrifuge train with 1N HCl and then with deionized water until residual chloride levels were <5 ppm. The polymer was isolated by steam precipitation followed by drying under hot nitrogen. The final dried resin weighed 3.0 lbs, had Mw=28656 daltons and PDI=2.4 by GPC vs PC standard, <1 ppm TEA, 0.61 ppm chloride ion, 41 ppm residual free BPA, and 0.12 ppm Fe.

Synthesis of 4-(2-(4-hydroxyphenyl)propan-2-yl)-2-methoxyphenol (aka, mono-methoxy BPA or guaiacol BPA)

A molten solution of phenol (1848 g, 19.65 mol), guaiacol (812 g, 6.55 mol), and acetone (120 g, 2.14 mol) at 50 C was fed downflow to a jacketed reactor containing 35 g of attached promoter IER catalyst (a monodispersed strongly acidic ion exchange resin with 2% divinylbenzene crosslinking, modified with ethylmercaptan promoter, 2.2 meg strong acid/g, 1.4 meg SH/g) with weighted hourly space velocity=1.0 while the reactor was held at 70 C. The reactor effluent was cooled to 40 C and filtered to remove the BPA-phenol adduct. The filtrate was then stripped to 170 C/20 ml torr and the residue crystallized from isopropyl alcohol. The filtrate from the isopropyl alcohol was stripped to dryness on a rotovap and the residue purified by column chromatography (eluting with 85% cyclohexane/15% ethyl acetate on silica gel) to give 63 g of a BPA:monomethoxyBPA:dimethoxyBPA mixture that was 18% BPA, 63% monomethoxyBPA, and 18% dimethoxyBPA by UPLC peak area.

Synthesis of BPA/monomethoxyBPA Copolymers Via Interfacial Polymerization

Run 1—10% guaiacol BPA: Methylene chloride (500 ml), deionized water (300 ml), BPA (13.2 g, 0.059 mol), monomethoxyBPA (1.58 g of the above mixture), p-cumylphenol (0.42 g, 0.002 mol) and triethylamine (0.18 ml, 0.0013 mol) were charged to a 2 L Morton flask equipped with mechanical agitation, pH controller, and chilled glycol condenser operating at 10-15 C. Gaseous phosgene (9 g, 0.09 mol) was introduced subsurface at 1 g/min. Aqueous 33 wt % NaOH was added as necessary to maintain reactor pH=9. The reactor was purged with nitrogen and the absence of residual phosgene confirmed with test paper. Agitation was stopped and the phases allowed to separate. The polymer-containing methylene chloride phase was removed and washed with 1N aqueous HCL (1×500 ml) and then with deionized water (3×500 ml). The polymer was isolated by hot water precipitation and the resulting resin powder was dried in air at 60 C overnight.

Polymer molecular weight of 24676 dalton vs BPA PC standard was determined by gel permeation chromatography. Glass transition temperature was measured as 148 C by differential scanning calorimetry. Proton NMR confirmed the incorporation of the monomethoxyBPA, which showed methoxy resonance at 3.78 ppm (singlet). A sample of the resin was digested in KOH/THF and the resulting monomers were analyzed by UPLC, showing a composition of 90 m % BPA, 7 m % monomethoxyBPA, 2 m % dimethoxyBPA, and 3 m % p-cumylphenol, indicating that no significant degradation of the monomethoxyBPA had occurred during polymerization.

Run 2—20% guaiacol BPA: Methylene chloride (500 ml), deionized water (300 ml), BPA (6.9 g, 0.030 mol), monomethoxyBPA (3.13 g of the above mixture), p-cumylphenol (0.27 g, 0.0013 mol) and triethylamine (0.12 ml, 0.0009 mol) were charged to a 2 L Morton flask equipped with mechanical agitation, pH controller, and chilled glycol condenser operating at 10-15 C. Gaseous phosgene (6 g, 0.06 mol) was introduced subsurface at 1 g/min. Aqueous 33 wt % NaOH was added as necessary to maintain reactor pH=9. The reactor was purged with nitrogen and the absence of residual phosgene confirmed with test paper. Agitation was stopped and the phases allowed to separate. The polymer-containing methylene chloride phase was removed and washed with 1N aqueous HCL (1×500 ml) and then with deionized water (3×500 ml). The polymer was isolated by hot water precipitation and the resulting resin powder was dried in air at 60 C overnight.

Polymer molecular weight of 17316 dalton vs BPA PC standard was determined by gel permeation chromatography. Glass transition temperature was measured as 142 C by differential scanning calorimetry. Proton NMR confirmed the incorporation of the monomethoxyBPA, which showed methoxy resonance at 3.78 ppm (singlet). A sample of the resin was digested in KOH/THF and the resulting monomers were analyzed by UPLC, showing a composition of 75 m % BPA, 17 m % monomethoxyBPA, 5 m % dimethoxyBPA, and 3 m % p-cumylphenol, indicating that no significant degradation of the monomethoxyBPA had occurred during polymerization.

Run 3—1% guaiacol BPA: Methylene chloride (23 L), water (8 L), BPA (4500 g, 19.8 mol), monomethoxyBPA (55 g of the above mixture), p-cumylphenol (135 g, 0.64 mol), triethylamine (40 ml) and sodium gluconate (10 g) was charged to a 75 L reactor equipped with mechanical agitation, condenser, and caustic scrubber vent system. Phosgene (2300 g, 23.2 mol) was added at a rate of 80 g/min to the reactor while 33 wt % caustic was added at a rate to maintain pH=10. The reactor contents were purged with nitrogen then transferred to another tank and centrifuged to remove the brine layer. The organic layer containing the polymer was washed on a centrifuge train with 1N HCl and then with deionized water until residual chloride levels were <5 ppm. The polymer was isolated by steam precipitation followed by drying under hot nitrogen. The final dried resin weighed 4.1 lbs, had Mw=27652 daltons and PDI=2.5 by GPC vs PC standard, <1 ppm TEA, 0.6 ppm chloride ion, <10 ppm residual free BPA, and <0.05 ppm Fe. The glass transition temperature was determined to be 153 C.

All of the patents and publications referenced herein are incorporated herein by reference in their entirety.

What is claimed is:

1. A method for preparing bisphenol A comprising combining phenol and acetone in the presence of a catalyst to form bisphenol A, wherein the phenol, the acetone or both are derived at least in part from a biosource, and wherein the phenol and/or the acetone contains at least 0.5 weight % of bio-derived impurities.

2. The method of claim 1, wherein the phenol contains one or more bio-derived impurities selected from the group consisting of 2-methylbenzofuran, 2-methoxyphenol, 2-methylphenol, 4-methylphenol (para-cresol) or 2-methoxy-4-methylphenol.

3. The method of claim 2, wherein the bisphenol A is crystallized as an adduct with phenol, further comprising the step of stripping phenol and one or more impurities from the bisphenol by desorption.

4. The method of claim 3, wherein the impurity includes at least 500 ppm 2-Methoxy-4-methylphenol.

5. The method claim 3, wherein the impurity includes at least 500 ppm 4-methylphenol (para-cresol).

6. The method of claim 3, wherein the phenol contains less than 5 weight % guaiacol.

7. The method of claim 3, wherein the phenol contains less than 10 weight % cresols.

8. The method of claim 2, wherein the impurity includes at least 500 ppm 2-Methoxy-4-methylphenol.

9. The method claim 2, wherein the impurity includes at least 500 ppm 4-methylphenol (para-cresol).

10. The method of claim 2, wherein the phenol contains less than 5 weight % guaiacol.

11. The method of claim 2, wherein the phenol contains less than 10 weight % cresols.

12. The method of claim 1, wherein the bisphenol A is crystallized as an adduct with phenol, further comprising the step of stripping phenol and one or more impurities from the bisphenol by desorption.

13. The method of claim 1, wherein the phenol is bio-derived.

14. The method of claim 13, wherein the phenol contains at least 1 wt % bio-derived impurities.

15. The method of claim 1, wherein the acetone is bio-derived.

16. A method of making BPA-containing polycarbonate, comprising the steps of:
   (1) obtaining a feedstock of bisphenol A formed in claim 1
   (2) treating the feedstock obtained in step (1) under phase transfer, melt, solid state, or any other polymerization process conditions sufficient to form BPA-containing polycarbonate, thereby forming BPA-containing polycarbonate.

17. The method of claim 16, wherein at least 80 weight % of the BPA incorporated in the polymer is bioderived material.

18. The method of claim 17, wherein the BPA-containing polycarbonate is a BPA homopolymer.

19. The method of claim 16, wherein at least 70% of the carbons in the polycarbonate are bioderived carbons.

20. A polycarbonate comprising BPA formed from bio-derived phenol, wherein at least 70% of the carbons in the polycarbonate are bioderived carbons.

21. The polycarbonate of claim 20, wherein at least 90% of the carbons in the polycarbonate are bioderived carbons.

22. The polycarbonate of claim 20, wherein 100% of the carbons in the polycarbonate are bioderived carbons.

23. A polycarbonate comprising BPA formed from bio-derived phenol, wherein at least 80 weight % of the BPA incorporated in the polymer is bioderived material.

24. The polycarbonate of claim 23, wherein 100 weight % of the BPA incorporated in the polymer is bioderived material.

25. A polycarbonate comprising BPA formed from bio-derived acetone, wherein the amount of bio-derived carbons in the polycarbonate is at least 17 weight %.

26. A polycarbonate formed by reaction of a bisphenol reagent, where the bisphenol reagent consists of 99 weight % bisphenol A and 1 weight % guaiacol bisphenol A.

* * * * *